United States Patent [19]

Darmory et al.

[11] 4,016,173
[45] Apr. 5, 1977

[54] OXINDOLE DIAMINES
[75] Inventors: Franklin P. Darmory, Ardsley; Marianne DiBenedetto, Pleasantville, both of N.Y.
[73] Assignee: Ciba-Geigy Corporation, Ardsley, N.Y.
[22] Filed: Sept. 26, 1975
[21] Appl. No.: 617,223

Related U.S. Application Data
[63] Continuation of Ser. No. 443,287, Feb. 19, 1974, abandoned, which is a continuation-in-part of Ser. No. 204,301, Dec. 2, 1971, abandoned.
[52] U.S. Cl. .................. 260/325 R; 260/78 R
[51] Int. Cl.$^2$ ...................... C07D 209/38
[58] Field of Search .................. 260/325 R

[56] References Cited
UNITED STATES PATENTS
3,705,869  12/1972  Darmory et al. ............ 260/30.4 N FOREIGN PATENTS OR APPLICATIONS
468,640  7/1937  United Kingdom ........... 260/325 R OTHER PUBLICATIONS
Wexler et al., "Chem. Abstracts", vol. 75, p. 5 No. 49654d (1971).
Stolle et al., "Chem. Abstracts", vol. 27, p. 1347 (1933).

Primary Examiner—Dolph H. Torrence
Attorney, Agent, or Firm—Charles M. Vanecek

[57] ABSTRACT

Oxindole diamines are prepared by a process comprising reacting an isatin derivative with an anilide and a Friedel Crafts catalyst in an inert solvent at a temperature of from 50° to 150° C with subsequent hydrolysis of the reaction product to yield the oxindole diamine. These compounds are useful in preparing polyimide type polymers.

2 Claims, No Drawings

OXINDOLE DIAMINES

This is a continuation of application Ser. No. 443,287 filed on Feb. 19, 1974, now abandoned, which is a continuation-in-part of Ser. No. 204,301, filed 12/2/71 now abandoned.

DETAILED DISCLOSURE

This invention relates to novel oxindole diamine derivatives and to a process for the preparation of these compounds.

More specifically, the oxindole diamine derivatives of this invention are represented by the formula:

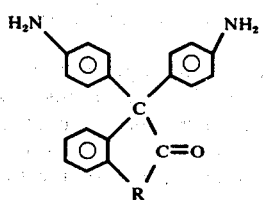

I wherein R is N-(lower)alkyl or N-aryl.

The (lower) alkyl groups employed herein are both straight or branched chain alkyl groups having up to six carbon atoms. Examples of such groups are methyl, ethyl, propyl, isopropyl, butyl, t-butyl, pentyl, hexyl, and the like. The aryl groups employed include phenyl; phenyl substituted with one or more alkyl groups such as methyl, ethyl, and propyl or with one or more halogen groups such as chlorine or bromine and nitro groups; naphthyl, anthryl, phenanthryl and the like.

In preferred oxindole diamines of this invention R is N-aryl. Especially preferred is 3,3-di-(p-aminophenyl)-1-phenyloxindole.

The compounds of formula I may be prepared by the following procedure which comprises a. reacting an isatin derivative of the formula

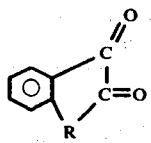

II wherein R is N-(lower)alkyl or N-aryl, with an anilide of the formula

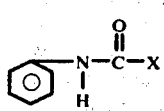

III wherein X is alkyl of from 1 to 6 carbon atoms, aryl or anilino, and a Friedel Crafts catalyst in an inert solvent at a temperature of from about 50° to 150° C wherein said isatin derivative is present in an amount ranging from 1 to 15% by weight of the total reaction mixture, said anilide is present in at least a mole equivalent amount based on the amount of the isatin derivative, and said Friedel Crafts catalyst is present in an amount ranging from 2 to 10 mole equivalents based on the amount of said isatin derivative present in the reaction mixture;

b. precipitating resultant reation product from step (a);

c. hydrolyzing said reaction product in an aqueous acidic solution.

The isatin derivatives wherein R is N-aryl and N-alkyl may be prepared as indicated in Beilstein, 21, page 447; 1st Supplement page 355; 2nd Supplement, page 337. The reference teaches the preparation of 1-phenyl isatin by reacting oxalyl chloride with diphenylamine. By following the procedure of this reference but substituting other aryl or alkylsubstituted phenylamines for the diphenyl amine, the appropriate isatin derivative is obtained. Thus, amines which may be substituted for diphenylamine include n-methylaniline, N-ethylaniline, N-propylaniline, N-butylaniline, N-isopropylaniline, N-hexylaniline, and the like as well as N-anthrylaniline, N-naphthylaniline and the like.

The process of this invention may be presented by the following chemical reaction

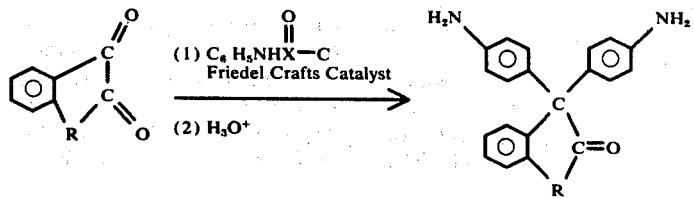

wherein R and X are as defined previously.

The reaction as indicated in step (1) is carried out at a temperature of from 50° to 150° C and preferably from 90° to 120° C.

Most Friedel Crafts type solvents which have boiling points within the temperature range above stated or higher and which are inert to the reactants employed are suitable for this reaction.

Examples of suitable solvents are tetrachloroethane, trichloroethane, dichloroethane, nitrobenzene, and the like.

In the second step of the reaction, the reacted anilide is hydrolyzed to yield the oxindole diamine derivative. The hydrolysis is carried out at reflux temperature in the aqueous acidic solution. Acids which may be used include sulfuric acid, hydrochloric acid, toluene sulfonic acid and the like, alone or in combination with acetic acid. The preferred aqueous acidic solution consists of water, sulfuric acid and acetic acid.

The concentration of the isatin derivative and the reaction mixture may range from 1 to 15% by weight of the total reaction mixture and preferably in the range of from 2 to 7%.

It is generally preferable to have a slight excess of anilide in the reaction mixture. Thus, at least 1 to 5 mole equivalents of anilide is used per mole equivalent of the isatin derivative and preferably from 1 to 2 mole equivalents. The amount of Friedel-Crafts catalyst present in the reaction consists of from 2 to 10 mole equivalents based on the amount of the isatin derivative and preferably from 2 to 6 mole equivalents.

Examples of the Friedel-Crafts catalyst are those which are well known in the art and include aluminum chloride, aluminum bromide, ferric chloride, ferric bromide, zinc chloride, titanium tetrachloride, boron trifluoride, hydrogen fluoride, stannic chloride, sulfuric acid, polyphosphoric acid, and the like.

Exemplary of the anilide compounds of formula III wherein X is alkyl of from 1 to 6 carbon atoms are acetanilide, propionanilide, isopropionanilide, butyranilide, pentananilide, hexananilide, and the like; and wherein X is aryl are benzanilide, naphthanilide, and the like.

In a most preferred embodiment of the process of this invention, a solution of 0.05 equivalents of the isatin derivative, 0.06 mole equivalents of the carbanilide, and 0.30 moles of aluminum chloride in 200 ml. of nitrobenzene are maintained at 100° C for about 12 hours. The cooled solution is poured into one liter of ice water and 600 ml. of hexane to precipitate the product. After filtering, the product is suspended in 200 ml. of acetic acid, 5 ml. of water, and 20 ml. of sulfuric acid. This solution is refluxed for approximately 24 hours, cooled and filtered. This refluxing hydrolyzes the reacted anilide and yields the desired oxindole diamine derivative. The filtrate containing the oxindole diamine derivative is neutralized with sodium carbonate and the solution concentrated in vacuo and taken in about 300 ml. of boiling 1N hydrochloric acid. This solution is diluted in about 300 ml. of water, cooled to about 5° C, filtered, and made basic with ammonia to precipitate the product. The product is collected and may be recrystallized from a dioxane hexane solution to yield the pure oxindole diamine derivative.

The oxindole diamine derivatives of this invention may be used to prepare high temperature polyimides. The polyimides may be prepared by reacting the oxindole diamine derivatives with an aromatic dianhydride at room temperature in a suitable solvent such an N-methylpyrrolidone. The polyimide is formed by heating the polyamic acid at 160° to 240° C for at least an hour. Typical of the aromatic dianhydrides which may be used are 3,4,3',4'-tetracarboxylic benzophenone dianhydride and pyromellitic dianhydride. The polyimides so prepared display excellent physical, chemical and electrical properties which render them capable of being used as adhesives, laminating resins, films, fibers, coatings for decorative and electrical purposes such as wire enamels, and molding compounds.

To further illustrate the nature of this invention and process employed in preparing the oxindole diamines, the following examples are given below:

EXAMPLE 1

3,3-di-(p-aminophenyl)-1-phenyloxindole a. Preparation of 1-phenylisatin

To a solution of 1590 g (12.5 moles) of oxalyl chloride in 20 l. of dry methylene chloride at 0° was added, with stirring, a solution of 2115 g (12.5 moles) of diphenylamine in 10 l. of dry methylene chloride.

After the addition was completed, the mixture was brought to room temperature and stirred for 18 hours. The solution was then concentrated in vacuo. The residual oil was taken up in 30 l. of nitrobenzene, and this solution was treated with 3340 g (25 moles) of aluminum chloride. This solution was then heated, with stirring, at 120° C. for 4 hours. Vigorous hydrogen chloride evolution occurs throughout this operation.

b. Preparation of 3,3-di-(p-aminophenyl)-1-phenyloxindole

The cooled solution from step (a) was treated with 3000 g (14.1 moles) of s-diphenylurea and an additional 3340 g (25 moles) of aluminum chloride. The mixture was maintained, with stirring, at 100° C for 18 hours.

The cooled solution was poured, with vigorous stirring, into a mixture of 100 l. of hexane and 100 l. of water. The precipitated solid was collected and washed with 10 additional liters of hexane to remove all residual nitrobenzene.

The collected solid was suspended in 50.1 of acetic acid and treated with 0.5 l. of water and 9.1 of concentrated sulfuric acid. The mixture, which became homogeneous on heating, was then refluxed for 18 hours.

The cooled solution was filtered, and the filter cake was washed with 2 l. of acetic acid. The combined filtrates were then treated carefully with 16 kg. of sodium carbonate and concentrated, in vacuo, to dryness. The remaining solids were taken up in 100 l. of boiling 1 N hydrochloric acid. The solution was cooled and filtered.

The filtrate was made basic with concentrated ammonium hydroxide and the precipitated solid was collected.

The crude diamine was recrystallized from 50 l. of methyl cellosolve with Darco decolorization (1 kg.) and water (70 l. precipitation. The product had a melting point of 276°–278° C.

Calc. for $C_{26}H_{21}N_3O$: Calculated: %C, 79.77; %H, 5.41; %N, 10.74. Found: %C, 78.87; %H, 5.65; %N, 10.45.

By essentially following the above procedure in steps (a) and (b) and substituting for diphenyl amine in step (a), an equivalent amount of the following:
1. N-methylaniline
2. N-propylaniline
3. N-pentylaniline
4. N-hexylaniline there is respectively obtained:
1. 3,3-di-(p-aminophenyl)-1-methyloxindole
2. 3,3--di-(p-aminophenyl)-1-propyloxindole
3. 3,3-di(p-aminophenyl)-1-pentyloxindole
4. 3,3-di-(p-aminophenyl)-1-hexyloxindole In each of the procedures of example 1 the respective oxindole diamine derivatives may be prepared by substituting for s-diphenylurea, an equimolar equivalent amount of the following anilides: acetanilide, propionanilide, pentananilide, hexananilide, and benzanilide.

EXAMPLE 2

To a solution of 0.01 mole of 3,3-di-(p-aminophenyl)-1-phenyl-oxindole in 45 ml of distilled N-methylpyrrolidone, under nitrogen, was added 3,222 g. (0.01 mole) of 3,4,3',4'-tetracarboxylic benzophenone dianhydride (BTDA) in portions over a 15 minute period. The solution was then stirred for about 15 hours at room temperature and under nitrogen.

The reaction vessel was then immersed in a 200° C oil bath. Thermal equilibrium was rapidly established at 185° C, and the reaction mixture was maintained at that temperature for 3 hours. The reaction vessel was swept out by a strong nitrogen flow during the first few minutes of the imidization so as to remove all traces of water formed in the reaction. The vessel was again swept out after 10 minutes, 30 minutes and 1 hour.

A soluble polyimide was obtained which had an intrinsic viscosity of 0.60 in at 25° C and a glass transition temperature of 355° C as determined by torsional braid analysis.

Films were cast from the polyimide solution onto glass and aluminum and heated in a forced air oven at 200° C for several hours to drive off the solvent. The coatings obtained were clear, tough, and flexible and all coatings were able to be dissolved in the solvent from which they were prepared.

When the same coatings were heated to 300° C for one half hour, they were still tough, clear and flexible; however, they were no longer soluble.

The polyimide was aged isothermally in a forced air oven at 300° C. The percent weight loss was minor after 600 hours.

The polyimide powder which is obtained by precipitation from solution with acetone and dried in a vacuum oven at 80° C may be molded by heating the powder in a cavity mold at 410° C and a pressure of about 5000 psi.

What is claimed is:
1. A compound having the formula:

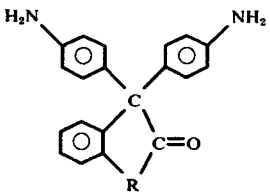

wherein
R is a member selected from N-phenyl; N-phenyl substituted with at least one methyl, ethyl, propyl, chloro, bromo or nitro group; N-naphthyl, N-anthryl; and N-phenanthryl.
2. A compound according to Claim 1 which is 3,3-di-(p-aminophenyl)-1-phenyloxindole.

* * * * *